(12) United States Patent
Mihalik

(10) Patent No.: US 9,597,140 B2
(45) Date of Patent: Mar. 21, 2017

(54) ACCESSORY TO ALLOW SENSING AT BALLOON INTERFACE

(71) Applicant: Medtronic CryoCath LP, Toronto (CA)

(72) Inventor: Teresa Mihalik, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 401 days.

(21) Appl. No.: 14/169,269

(22) Filed: Jan. 31, 2014

(65) Prior Publication Data

US 2015/0216580 A1   Aug. 6, 2015

(51) Int. Cl.
*A61B 5/04*   (2006.01)
*A61B 18/02*  (2006.01)
*A61B 5/01*   (2006.01)
*A61B 5/042*  (2006.01)
*A61B 18/14*  (2006.01)
(Continued)

(52) U.S. Cl.
CPC ............... *A61B 18/02* (2013.01); *A61B 5/01* (2013.01); *A61B 5/042* (2013.01); *A61B 18/1492* (2013.01); *A61B 5/4848* (2013.01); *A61B 5/6853* (2013.01); *A61B 5/6859* (2013.01); *A61B 2018/0022* (2013.01); *A61B 2018/00357* (2013.01); *A61B 2018/00577* (2013.01); *A61B 2018/00648* (2013.01); *A61B 2018/00797* (2013.01); *A61B 2018/00821* (2013.01); *A61B 2018/00839* (2013.01); *A61B 2018/0212* (2013.01); *A61B 2018/0262* (2013.01)

(58) Field of Classification Search
CPC ............ A61B 2018/00214; A61B 2018/00267
See application file for complete search history.

(56) References Cited

U.S. PATENT DOCUMENTS 5,833,625 A   11/1998  Essen-Moller
6,514,249 B1 *  2/2003  Maguire ................ A61B 18/00
                                                    606/37
(Continued)

OTHER PUBLICATIONS

International Search Report and Written Opinion dated Mar. 10, 2015, for corresponding International Application No. PCT/CA2014/000892; International Filing Date: Dec. 17, 2014 consisting of 9-pages.

*Primary Examiner* — Joseph Stoklosa
*Assistant Examiner* — Luther Behringer
(74) *Attorney, Agent, or Firm* — Christopher & Weisberg, P.A.

(57) ABSTRACT

A device, system and method for temperature-based lesion formation assessment and mapping functionality using an accessory usable with an over-the-wire balloon catheter. The device may include a first annular element, a plurality of wires coupled to the first annular element, and a second annular element, the plurality of wires passing from the first annular element through the second annular element and into an elongate wire conduit coupled to the second annular element. At least one of the plurality of wires may include at least one temperature sensor and/or at least one mapping electrode. The first annular element coupled to an outer surface of a sheath. As a balloon catheter is advanced out of the sheath lumen, the distal tip of the catheter engages the second annular element and pushes the wires out of the sheath lumen, everting them over the balloon of the catheter.

11 Claims, 10 Drawing Sheets

(51) Int. Cl.
  *A61B 18/00* (2006.01)
  *A61B 5/00* (2006.01)

(56) References Cited

U.S. PATENT DOCUMENTS

| | | |
|---|---|---|
| 7,972,330 B2 | 7/2011 | Alejandro et al. |
| 2005/0096647 A1 | 5/2005 | Steinke et al. |
| 2006/0271093 A1 | 11/2006 | Holman et al. |
| 2009/0299355 A1 | 12/2009 | Bencini et al. |
| 2009/0306582 A1 | 12/2009 | Granada et al. |
| 2010/0217304 A1 | 8/2010 | Angel et al. |
| 2012/0071870 A1 | 3/2012 | Salahieh et al. |

\* cited by examiner

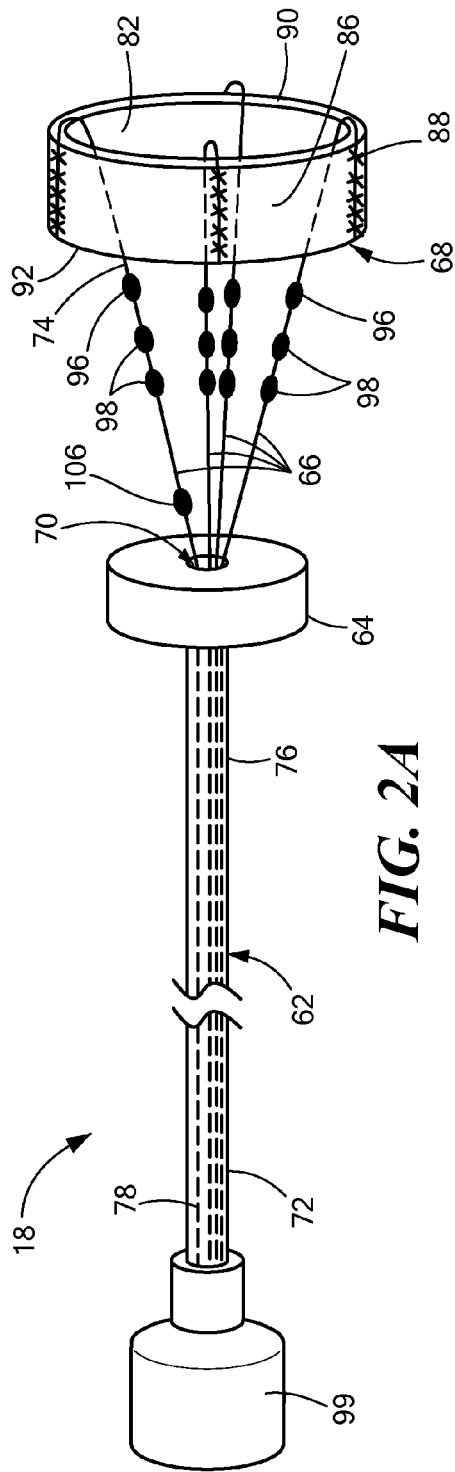
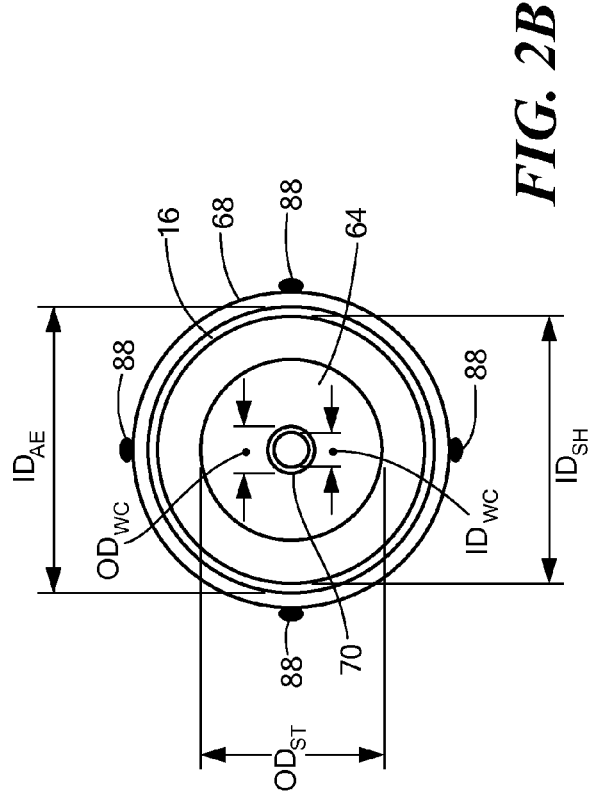
FIG. 2A
FIG. 2B

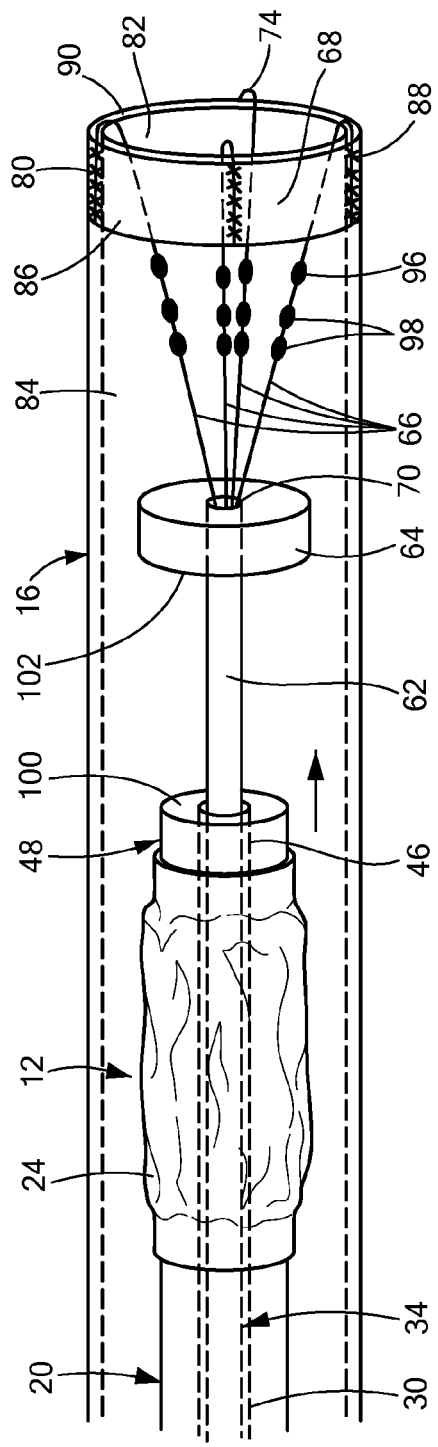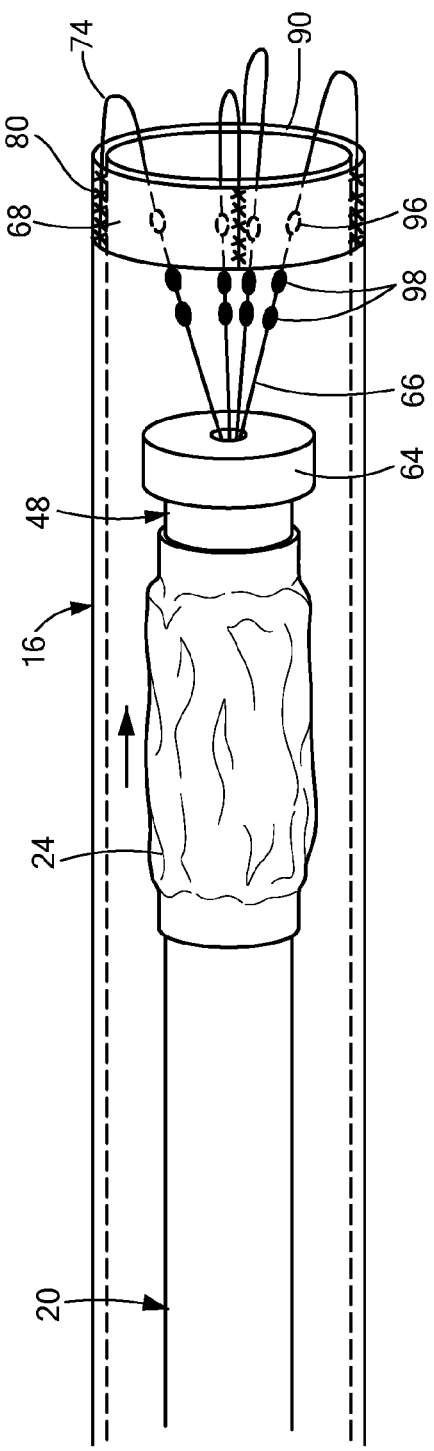

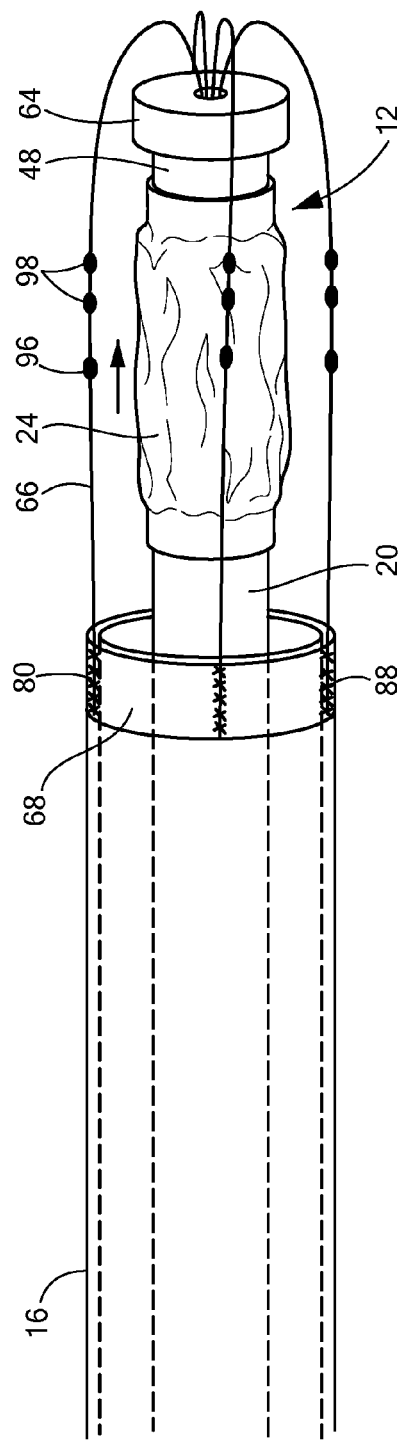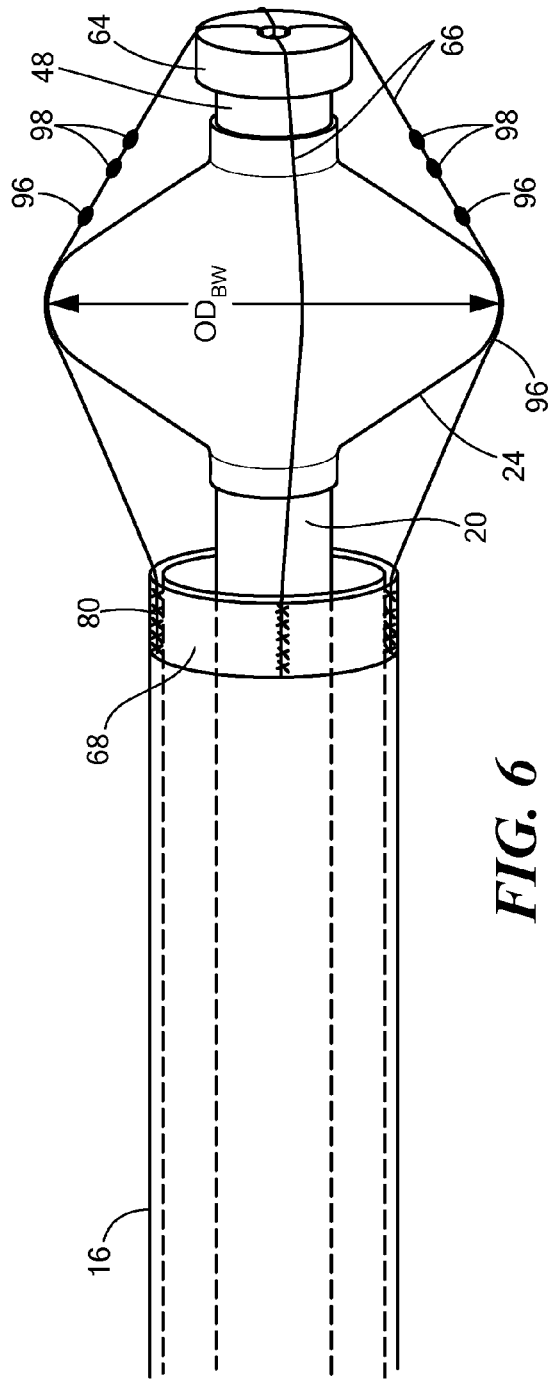
FIG. 5
FIG. 6

ACCESSORY TO ALLOW SENSING AT BALLOON INTERFACE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for a cryoablation system and device that allows for accurate temperature-based lesion formation assessment and mapping functionality using a relatively inexpensive catheter accessory that may be used on any aftermarket, over-the-wire balloon catheter.

BACKGROUND OF THE INVENTION

A cardiac arrhythmia is a condition in which the heart's normal rhythm is disrupted. There are many types of cardiac arrhythmias, including supraventricular arrhythmias that begin above the ventricles (such as premature atrial contractions, atrial flutter, accessory pathway tachycardias, atrial fibrillation, and AV nodal reentrant tachycardia), ventricular arrhythmias that begin in the lower chambers of the heart (such as premature ventricular contractions, ventricular tachycardia, ventricular fibrillation, and long QT syndrome), and bradyarrhythmias that involve slow heart rhythms and may arise from disease in the heart's conduction system.

Catheter ablation is commonly used to treat a variety of cardiovascular conditions, such as cardiac arrhythmias, atrial fibrillation, and other irregularities in the transmission of electrical impulses through the heart. This minimally invasive surgical technique may involve the use of tip electrodes, electrode arrays, cryoballoons, and/or other ablating elements to create lesions or other anatomical effects that disrupt or block electrical pathways through the targeted tissue.

The success of this procedure depends largely on the quality of the lesion(s) created during the procedure. In theory, the most accurate way to assess lesion formation is by monitoring the temperature of the tissue being ablated. However, measuring the temperature of treated tissue during a procedure may be difficult or impossible using known devices and methods, and integrating temperature sensors into the ablation device can increase the size, complexity, and cost of the device. Further, methods that measure temperature within the cryoballoon to approximate the temperature of treated tissue may not take into account the tissue type and response to treatment, and can be very inaccurate. Likewise, temperature-time assessment methods may be based on a one-size-fits-all model that does not take into account the type and depth of tissue, and may be subject to noise in the temperature data.

Further, in the treatment of cardiac arrhythmias, a specific area of cardiac tissue having aberrant electrical activity (e.g. focal trigger, slow conduction, excessively rapid repolarization, fractionated electrogram, etc.) is typically identified first before subsequent treatment. This process, sometimes referred to as localization or mapping, can include obtaining unipolar or bipolar electrograms, or monophasic action potential ("MAP") electrograms of a particular cardiac region. MAP signals may be obtained by temporarily depolarizing selected tissue, which responsive electrical activity being recorded or otherwise monitored for an indication of local depolarization timing, refractory period duration, and any aberrant electrical activity. After mapping and diagnosing aberrant tissue, a physician may decide to treat the patient by ablating the tissue. Accurate mapping of the cardiac tissue using bipolar, unipolar, or MAP electrogram signals can reduce the number of ablations necessary to treat an aberrant electrical pathway, and can make the executed ablations more effective. Additionally, MAP recordings can substantially improve the ability to determine the timing of local tissue activation, which is often ambiguous when recorded using standard intracardiac electrodes.

Presently, this procedure may require mapping an area of tissue with a first mapping device. Once an optimal ablation site is identified, the mapping device is withdrawn and replaced with an ablation device. However, this practice may increase the chances of patient injury or procedure complications, and may disadvantageously increase the total time needed to treat a condition. Alternatively, presently known devices may include mapping and ablation functionality in a single device, which may reduce procedure time and complexity by eliminating the need to employ separate mapping and ablation devices for each task. Combination mapping and ablation devices also increase ablation accuracy, because once aberrant tissue (the "target tissue") is found, ablation can begin immediately without having to remove the mapping device and relocating the target tissue with the ablation device. However, such devices may require complicated manufacturing steps and expensive materials, may present insulation problems between mapping and ablation electrodes, and the devices themselves may be prohibitively expensive for some surgeons.

Therefore, it is desirable to provide a cryoablation system, device, and method that allows for accurate temperature-based lesion formation assessment and mapping functionality using a relatively inexpensive catheter accessory that may be used on any aftermarket, over-the-wire balloon catheter.

SUMMARY OF THE INVENTION

The present invention advantageously provides a method and system for evaluating tissue, such as by providing an accessory that allows for temperature-based lesion formation assessment and mapping functionality. The accessory may be used on an aftermarket, over-the-wire balloon catheter. In one embodiment, the accessory may include a first annular element, a plurality of wires coupled to the first annular element, and a second annular element, the plurality of wires passing from the first annular element through the second annular element. The accessory may further include an elongate wire conduit coupled to the second annular element, with the plurality of wires passing through the second annular element and into the wire conduit. At least one of the plurality of wires may include at least one temperature sensor and/or at least one mapping electrode, and may further include at least one reference electrode. For example, the accessory may include four wires with each wire including a temperature sensor and a mapping electrode and, optionally, one of the wires may include a reference electrode. The accessory may further include a sheath having a distal portion, a proximal portion, and a lumen therebetween, and the sheath lumen may be sized to receive a balloon catheter within when the balloon is deflated. The first annular element may be coupled to an outer surface of the distal portion of the sheath, and the second annular element and at least a portion of each wire may be disposed within the sheath lumen. The medical device may be an over-the-wire device, such as a balloon catheter, having a lumen that is sized to receive the elongate wire conduit. A proximal face of the second annular element may be configured to be engageable with a distal tip of a medical device. For example, the proximal face of the second annular element may be configured to be matably engageable with a distal tip of the medical device.

A medical system for evaluating tissue may generally include an elongate sheath having a proximal portion, a distal portion, and a lumen therebetween, a first annular element coupled to an outer surface of the distal portion of the sheath, a plurality of wires coupled to the first annular element, at least one of the plurality of wires including at least one sensor element, an elongate wire conduit disposed within the sheath lumen, the wire conduit having a proximal portion, a distal portion, and a lumen therebetween, and a second annular element coupled to the distal portion of the wire conduit, at least a portion of each of the plurality of wires passing through the second annular element and being disposed within the lumen of the wire conduit. The at least one sensor element may include a temperature sensor and/or a mapping electrode. Further, at least one of the plurality of wires may include a reference electrode. For example, each wire may include one or more temperature sensors and one or more mapping electrodes. The first annular element may include a distal edge, a proximal edge, an inner surface, and an outer surface, and each of the plurality of wires may include a proximal portion and a distal portion. A first portion of the distal portion of each of the plurality of wires may be coupled to the outer surface of the first annular element, a second portion of the distal portion of each of the plurality or wires may pass over the distal edge of the annular element, and a third portion of the distal portion of each of the plurality of wires may pass within the annular element proximate the inner surface of the annular element. The second annular element may include a proximal face and a distal face, the proximal face being configured to be releasably engageable with a distal tip of a medical device. The system may further include a control unit including a processor, the processor being configured to receive signals from the at least one sensor element. For example, the processor may cause the control unit to generate an alert based at least in part on signals received from the at least one sensor element.

A method for evaluating tissue may generally include advancing a balloon catheter having an uninflated balloon through a lumen of a sheath, the sheath including a first annular element coupled to a distal portion of the sheath, a plurality of wires coupled to an outer surface of the first annular element, and a second annular element coupled to an elongate wire conduit, at least a portion of each of the plurality of wires being disposed through the second annular element and within the wire conduit, the wire conduit, second annular element, and at least a portion of each of the plurality of wires being disposed within the sheath lumen; releasably engaging a distal tip of the balloon catheter with the second annular element; advancing the balloon catheter through the sheath lumen until the uninflated balloon, the second annular element, and at least a portion of each of the plurality of wires are located distal to the distal portion of the sheath; and inflating the balloon, at least a portion of each of the plurality of wires being disposed over the inflated balloon. At least one of the plurality of wires may include at least one sensing element, and the method may further include recording a physiological measurement with the at least one sensing element. The at least one sensing element may be a temperature sensor or a mapping electrode. For example, each wire may include both a temperature sensor and a mapping electrode. One of the plurality of wires may also include a reference electrode. The method may further include retracting the balloon catheter, the second annular element, and at least a portion of each of the plurality of wires within the sheath lumen; and further retracting the balloon catheter within the sheath lumen until the distal tip of the balloon catheter disengages from the second annular element.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2A shows a side perspective view of a balloon catheter accessory including temperature sensing and/or mapping functionality;

FIG. 2B shows an anterior view of a balloon catheter accessory including temperature sensing and/or mapping functionality;

FIGS. 3-7 show a series of steps for deploying a balloon catheter in use with a balloon catheter accessory;

DETAILED DESCRIPTION OF THE INVENTION

Figure 1:
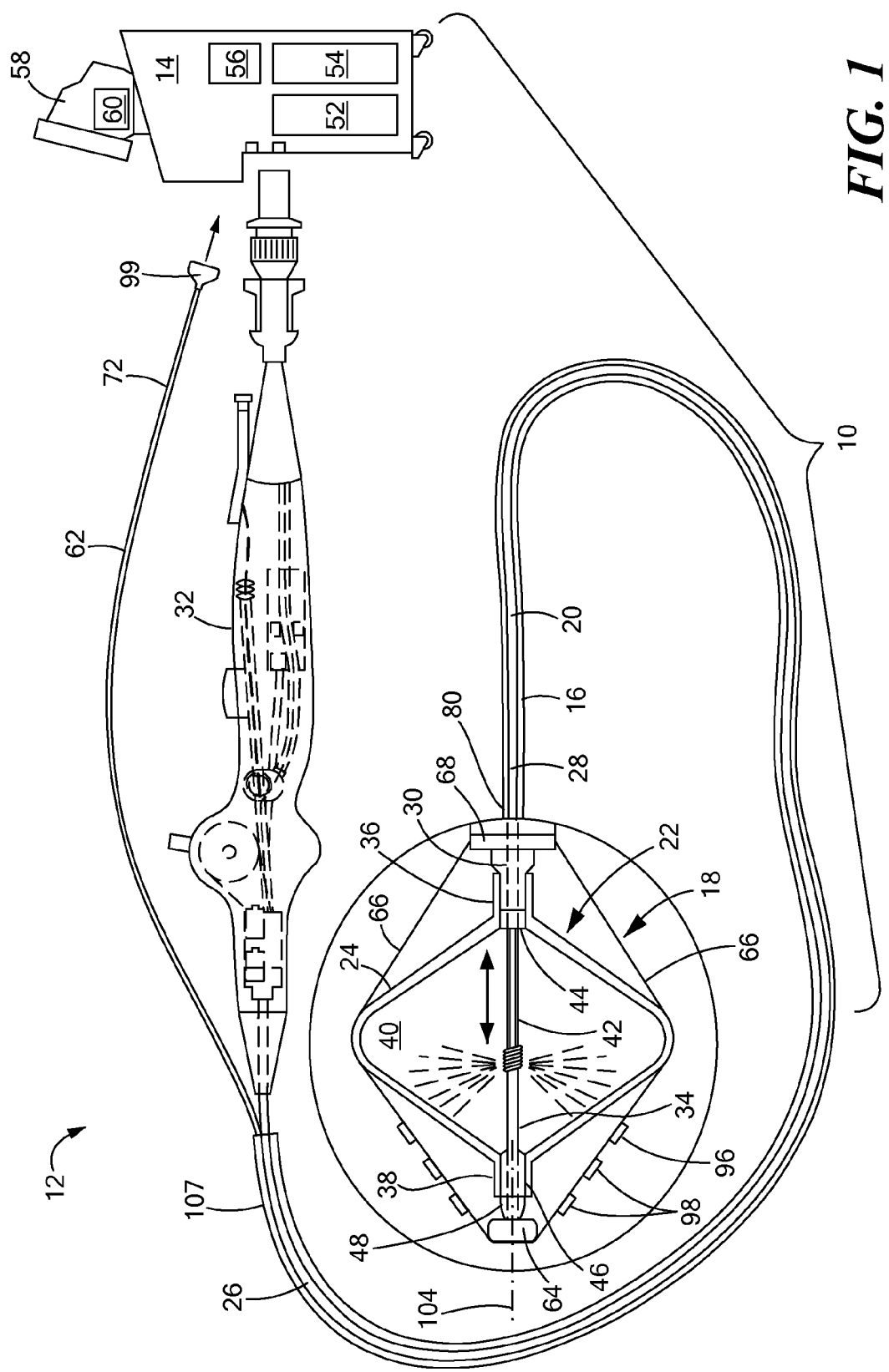
FIG. 1 shows an exemplary medical system including an over-the-wire balloon catheter.

The present invention provides a cryoablation system, device, and method that allows for accurate temperature-based lesion formation assessment and mapping functionality using a relatively inexpensive catheter accessory that may be used on any aftermarket, over-the-wire balloon catheter. Referring now to the figures, which are not necessarily drawn to scale and are not intended to limit the scope of the invention, in which similar elements in different drawings are numbered with like reference numbers, an exemplary medical system 10 is shown in FIG. 1. The system 10 may generally include an over-the-wire medical device 12 that may be coupled to a control unit 14 or operating console and a modified sheath, including a standard sheath 16 to which an accessory 18 having temperature sensing and/or mapping functionality is coupled or attached. The medical device 12, for example, a cryoablation device as shown in FIG. 1, may generally include an elongate body 20 and one or more treatment elements 22 for energetic, therapeutic and/or investigatory interaction between the medical device 12 and a treatment site. For example, the treatment element 22 may include an expandable element, such as a balloon 24. The treatment element 22 may deliver, for example, cryogenic therapy to a tissue area in proximity to a treatment region, including cardiac tissue and/or pulmonary vein tissue.

Continuing to refer to FIG. 1, the elongate body 20 may be passable through a patient's vasculature and/or proximate to a tissue region for diagnosis or treatment. Accordingly, the elongate body 20 may be composed of a biocompatible material that is sufficiently flexible to safely pass through tortuous pathways of the patient's vasculature. The elongate body 20 may define a proximal portion 26 and a distal portion 28, and may further include one or more lumens or conduits disposed within the elongate body 20 thereby providing mechanical, electrical, and/or fluid communication between the proximal portion of the elongate body 20 and the distal portion of the elongate body 20, such as a main lumen 30 as discussed in more detail below. The proximal portion 26 of the elongate body 20 may include a handle 32 having one or more knobs, levers, connectors, umbilicals, and other components used for steering, manipulating, and operating the device 12 and connecting the device 12 to the control unit 14.

The medical device 12 may further include an elongate guidewire lumen 34 at least partially disposed within a portion of the elongate body 20, such as the main lumen 30. The guidewire lumen 34 may extend or otherwise protrude from a distal end of the elongate body 20, and may be movable with respect to the elongate body 20 in longitudinal and rotational directions. That is, the guidewire lumen 34 may be slidably and/or rotatably moveable with respect to the elongate body 20. Alternatively, the guidewire lumen 34 may be affixed or coupled to the elongate body 20 such that the guidewire lumen 34 has a fixed position and is not slidably and/or rotatably moveable with respect to the elongate body 20.

The treatment element 22 may be located at a distal end of the device 12, and may, for example, be coupled to the distal portion 28 of the elongate body 20. As shown in FIG. 1, for example, the treatment element 22 may be a balloon 24, although it will be understood that the treatment element 22 may include more than one expandable element or balloon. The balloon 24 may include a proximal portion 36 and a distal portion 38, and may define an interior chamber or region 40 that is in fluid communication with a fluid delivery conduit 42 for providing fluid or coolant to the interior chamber 40 and a fluid recovery conduit 44 for the removal of expended coolant or other fluid from the interior 40 of the balloon 24. In the non-limiting embodiment shown in FIG. 1, the proximal portion 36 of the balloon 24 may be coupled to the distal portion 28 of the elongate body 20 and the distal portion 38 of the balloon 24 may be coupled to the distal portion 46 of the guidewire lumen 34, proximate a distal tip 48 of the device 12.

The proximal 36 and distal portion 38 of the balloon 24 may be coupled to the guidewire lumen 34 or elongate body 20 using, for example, a biocompatible adhesive. The balloon 24 may further include one or more layers providing for puncture resistance, radiopacity, or the like (for example, a second balloon disposed about the balloon 24), and may also be substantially electrically insulative. The balloon 24 may be composed of a compliant (for example, polyurethane [PU] of nylon elastomers) or non-compliant or semi-compliant material (for example, polyethylene terephthalate [PET] or nylon).

The device 12 may further include a fluid delivery lumen or conduit 42 that is in fluid communication with a fluid supply 52 to deliver a fluid (for example, coolant, saline, or other fluid) from the proximal portion 26 of the elongate body 20 and/or the control unit 14 to the distal portion 28 of the elongate body 20 and/or treatment element 22 of the device 12. Additionally, the device 12 may further include a fluid recovery lumen or conduit 44 that is in fluid communication with the scavenging system. The fluid delivery conduit 42 and fluid recovery conduit 44 may be included in or defined by either the elongate body 20 and/or guidewire lumen 34. If the fluid delivery conduit 42 is included in or defined by the guidewire lumen 34, the guidewire lumen 34 may include one or more fluid ejection ports for expelling fluid into the interior chamber 40 of the balloon 24 (not shown). Alternatively, the fluid delivery conduit is disposed within the elongate body 20, the fluid delivery conduit may extend into the balloon 24 in a parallel or substantially parallel fashion to the guidewire lumen 34, or may instead be coiled about or otherwise encircling or disposed about the guidewire lumen 34 (as shown in FIG. 1).

The system 10 may include one or more treatment or diagnostic sources coupled to the device 12 for use in an operative procedure, such as tissue ablation. For example, the control unit 14 may include a fluid supply 52 including one or more reservoirs for one or more coolants, cryogenic refrigerants, saline, or the like, an exhaust or scavenging system for recovering or venting expended fluid for reuse or disposal, as well as various control mechanisms. In addition to providing an exhaust function for the fluid supply 52, the control unit 14 may also include a fluid recovery reservoir 54, one or more pumps 56, valves, controllers or the like to recover and/or re-circulate fluid delivered to various fluid pathways of the medical device 12. A vacuum pump 56 in the control unit 14 may create a low-pressure environment in one or more conduits within the medical device 12 so that fluid is drawn into the conduits/lumens of the elongate body 20, away from the distal portion and toward the proximal portion of the elongate body 20.

The control unit 14 may also include one or more components for the manual and/or automatic regulation of the system, such as a computer 58 having a processor 60 for executing one or more algorithms for the automatic regulation of the device 12 before, during, and after an ablation procedure. For example, the processor 60 may be programmable to inflate and deflate one or more cryoballoons of the treatment element (such as according to a user-programmed duty cycle or an automated duty cycle), to regulate temperature of the treatment element, and/or to receive and interpret physiological measurement signals, for example, temperature and/or mapping signals, from the cryoablation device 12 or another device used as part of a medical procedure. Although various system components may be shown and described herein as being within the control unit 14, the term "control unit" as used herein refers to any system component other than the cryoablation device 12 and other devices that are passed into the patient to perform the medical procedure, regardless of whether the components are physically located within the control unit 14.

The medical system 10 may further include a catheter sheath 16 that may be inserted into the patient's vasculature prior to insertion of the ablation device 12, using methods known in the art. For example, as shown and described in more detail in FIGS. 3-7 and 10-14, the sheath 16 may be passed through the vasculature into an area proximate the target tissue (referred to as the target treatment site), such as the left atrium of the heart. Once the sheath 16 is positioned in the desired location, the ablation device 12 may be passed within the sheath 16, using methods known in the art, to the target treatment site. In many known systems and methods, the sheath 16 is removed or partially removed from the patient's body before an ablation procedure, leaving only the ablation device 12 proximate the target treatment site. In the present system, however, the sheath 16 is allowed to remain at a location proximate the treatment element 22 and the target treatment site, for reasons shown and described in more detail in FIGS. 1-14. The sheath 16 may or may not be in communication with the control unit 14.

Referring now to FIGS. 1-2B, an accessory having temperature sensing and/or mapping functionality that may be used in association with an over-the-wire medical device 12 is shown. The accessory 18 may generally include an elongate and flexible wire conduit 62, an annular stopper 64, a plurality of wires 66, and an annular anchor element 68. Although four wires 66 radially spaced approximately 90° apart are shown in FIGS. 2A and 2B, it will be understood that any number of wires 66 may be used. As shown in FIG. 2A, the wire conduit 62 may be coupled to or integrated with the stopper 64, with the stopper 64 having a larger outer diameter $OD_S$ than the outer diameter $OD_{WC}$ of the wire conduit 62. For example, the stopper 64 and wire conduit 62 may be manufactured from a single piece of material, such as Nitinol, stainless steel, polymer, or combinations thereof, or may be adhered or bonded to the wire conduit 62 using a biocompatible adhesive, bonding agent or welding or soldering, or the stopper 64 may be overmolded on the wire conduit 62. The material from which at least the wire conduit 62 is composed may be flexible enough to allow the wire conduit 62 to function as a guide wire lumen through the balloon. Further, the outer diameter $OD_{WC}$ of the wire conduit 62, and not the outer diameter $OD_S$ of the stopper 64, may be sized to pass within a lumen (for example, the main lumen 30) and/or the guidewire lumen 34 of the device 12. The outer diameter $OD_{ST}$ of the stopper 64 may be sized to pass within the inner diameter $ID_{SH}$ of the sheath 16.

The wire conduit 62 may be hollow and the stopper 64 may be annular with a center opening 70 having approximately the same inner diameter as the inner diameter of the wire conduit 62, such that at least a portion of each wire 66 passes through the opening 70 and into the wire conduit 62. For example, a portion of each wire 66 may be disposed within the wire conduit 62 from the stopper to a proximal end 72 of the wire conduit 62. The portions of the stopper 64 surrounding the center opening 70 may be composed of a low-friction material, may have rounded edges, and/or may include other features that promote free movement of the wires 66 over the stopper 64 without causing damage to or kinking or bending the wires 66. Further, a distal portion 74 of each wire 66 may extend out of and beyond a distal portion 76 of the wire conduit 62, and a proximal portions 78 of the wires 66 may be bundled within the proximal portion 72 of the wire conduit (as shown in FIGS. 1 and 2). The proximal portions 78 of the wires 66 may be in electrical communication with the control unit 14, and the processor 60 may be configured and programmable to receive and interpret temperature and/or mapping signal data from the accessory 18.

The anchor element 68 may be removably or permanently coupled to or affixed to a distal portion 80 of the sheath (for example, as shown in FIGS. 3-7). For example, the anchor element 68 may be composed of a magnetic metal and a distal portion 80 of the sheath 16 may be magnetized, such that an inner surface 82 of the anchor element 68 is magnetically coupled to distal portion 80 of the sheath 16. The strength of this coupling may depend on the strength of the magnetic attraction between the anchor element 68 and the sheath 16. In any case, however, the anchor element 68 may stay coupled to the sheath 16 while the sheath 16 remains inside the patient's body. Alternatively, the inner surface 82 of the anchor element 68 may be adhered to an outer surface 84 of the sheath 16, such as by the use of a biocompatible adhesive or bonding agent. Alternatively, the distal portion 80 of the sheath 16 may have a metal component to which an inner surface 82 of the anchor element 68 may be welded or anchored. As a non-limiting example, the inner diameter $ID_{AE}$ of the anchor element 68 may be between approximately 12 French and approximately 15 French.

At least a portion of the distal portion 74 of each wire 66 may be coupled to or affixed to an outer surface 86 of the anchor element 68. For example, a portion of each wire 66 may be anchored to or welded to the outer surface 86 of the anchor element 68 at one or more attachment points 88, depicted in FIG. 2A with hatch marks. From the attachment points 88, each wire 66 may pass over the distal edge 90 of the anchor element 68, pass within the anchor element 68 past the proximal edge 92, through the center opening 70 of the stopper 64, and into the wire conduit 62. Thus, the wires 66 may be disposed within the wire conduit 62, which, in turn, is within the sheath 16. In this manner, the wires 66 may be easily advanced out of the wire conduit 62 when the medical device 12 pushes on the stopper 64 and exits the sheath 16.

Each wire 66 may include at least one temperature sensor 96 and/or at least one mapping electrode 98. In the non-limiting embodiment shown in FIGS. 3-7, each wire may include one temperature sensor 96 and one mapping electrode 98. Additionally, at least one wire 66 may include a reference electrode 106, if monophasic action potential (MAP) electrograms are to be recorded. Otherwise, no reference electrode may be included. The temperature sensors 96 may be thermocouples or other sensors known in the art. Additionally or alternatively, the one or more sensors may be other types of sensors, such as pH sensors, pressure sensors, or the like. Each sensor 96 may be of any size and configuration that is suitable for lying against or in contact with an inflated balloon without rupturing or damaging the balloon, even when the balloon pushes the sensor 96 against myocardial tissue. Still further, each sensor 96 may be sized and shaped to ensure optimal contact with tissue during use.

The mapping electrodes 98 may be composed of a conductive metal and configured to record, for example, monopolar, bipolar, or monophasic action potential (MAP) electrograms. MAP electrograms, for example, may document the onset of local tissue depolarization, repolarization, and the general action potential morphology. The MAP signal may be generated by measurement between a mapping electrode 98 and a reference electrode 106. The reference electrode 106 may be in contact with the blood but generally not in contact with the myocardium, and the mapping electrode 98 may be in contact with the myocardium, with high enough local pressure to depolarize the underlying myocytes. To produce this increased local pressure, each mapping electrode 98 may be configured to protrude from the surface of the balloon 24 when the accessory 18 is engaged with the balloon 24. For example, the mapping electrodes may be dome shaped or have a rounded surface, may have one or more protuberances, or may have other geometries or textures that enhance contact with the myocardial tissue. Inflation of the balloon 24 against the mapping electrodes 98 may facilitate creating the necessary pressure between the mapping electrodes 98 and the target tissue. Further, although the mapping electrodes 98 may be positioned at any point along the distal portion 74 of each wire 66, the mapping electrodes 98 and temperature sensors 96 may be located at a position along the wire 66 that will be in contact with, or proximate, the area of the balloon 24 corresponding to the location where the pressure on the mapping electrodes 98 and temperature sensors 96 against the target tissue may be the greatest. As a non-limiting example, this location on a 28 mm balloon may be the area at which the balloon has a diameter of between approximately 15 mm and approximately 25 mm. When the balloon is pushed against the pulmonary vein ostium, the balloon may become at least partially compressed, giving the anterior portion of the balloon a somewhat conical shape. Although the distal tip of the device 12 may be advanced to a distance within the pulmonary vein, most of the balloon, including the portion anterior of the widest balloon outer diameter $OD_{BW}$, may remain in contact with the pulmonary vein ostium. Thus, optimal placement of the electrodes 98 and sensors 96 may be anterior to the widest outer diameter $OD_{BW}$, but proximal of the distal tip 48 of the device 12.

The proximal portion 72 of the wire conduit 62 and or the proximal portions 78 of the wires 66 may collectively be in electrical communication with an electrical connector 99 that is connectable to the control unit 14. However, the proximal portion 72 of the wire conduit 62 may be removably coupled to the connector 99 to allow the medical device 12 to be advanced over the wire conduit 62. The control unit 14, for example, the processor 60, may be configured and programmable to receive and interpret temperature and/or mapping signal data from the one or more temperature sensors 96 and/or mapping electrodes 98 through the wires 66. The processor 60 may be programmable to execute an algorithm that uses the received data to suggest to the user and/or automatically cause the control unit 14 to carry out a particular command, such as increasing the flow of coolant into the balloon 24, increasing the temperature of the balloon 24, inflate or deflate the balloon 24, display to the user an image of the patient's heart on which suggested or recommended ablation locations are shown, disable the temperature sensors 96, or other function that may enhance the effectiveness of the ablation or treatment procedure. Further, the processor 60 may be configured and programmable to cause the control unit 14 to broadcast an audible or visual alert to the user, which may notify the user that, based at least in part on signals received from the one or more temperature sensors 96 and/or mapping electrodes 98, the device 12 is at an optimal ablation site, is not at an optimal ablation site, that ablation depth is sufficient to create a permanent lesion, that ablation depth may have reached non-target tissue, or any of a variety of indications relating to the ablation or treatment procedure.

Referring now to FIGS. 3-7, a series of steps for deploying a balloon catheter in use with a balloon catheter accessory are shown. In an exemplary method of deployment, the anchor element 68 of the accessory 18 may be coupled to the distal portion 80 of the sheath 16, with the wires 66, stopper 64, and wire conduit 62 being disposed within the sheath 16. As shown in FIG. 3, an over-the-wire balloon catheter 12 may be advanced over the wire conduit 62 with the balloon 24 in an uninflated configuration. At this stage, the stopper 64 may be at a location proximal to the anchor element 68. The balloon catheter 12 may be advanced over the wire conduit 62 until the distal tip 48 of the device 12 comes into contact with the stopper 64. As is shown and described in more detail in FIGS. 8A-9B, at least a portion of the stopper 64 may have a configuration that is matable with the device distal tip 48. Alternatively, the device distal tip 48 may have an annular distal face 100 that encircles the distal opening of the guidewire lumen 34, and the stopper 64 may include an annular proximal face 102 that encircles the outer diameter of the wire conduit 62, both of which faces 100, 102 being substantially orthogonal to the longitudinal axis 104 of the device 12. As shown in FIGS. 3-7, the distal face 100 of the device distal tip 48 may abut the proximal face 102 of the stopper 64. No matter the configuration of the interface between the device distal tip 48 and the stopper 64, further advancement of the device 12 over the wire conduit 62 may advance the stopper 64 through the sheath 16 and out the distal portion 80 of the sheath 16 (as shown in FIG. 4).

As shown in FIGS. 4 and 5, advancement of the stopper 64 within the sheath 16 may cause the wires 66 to protrude distally from the anchor element 68 as they are pushed away from the distal edge 90. However, at least a portion of the distal portion 74 of each wire 66 may remain affixed to the outer surface 86 of the anchor element 68 at the attachment points 88. Likewise, the anchor element 68 may remain coupled to the distal portion 80 of the sheath 16.

As shown in FIG. 6, once the balloon 24 has been advanced past the distal portion 80 of the sheath 16, the balloon 24 may be inflated, such as by the initiation of flow of a fluid (for example, a coolant) through the fluid delivery conduit 42 from the fluid supply 52 into the interior chamber 40 of the balloon 24. The distal portion 74 of each wire 66 that is exposed from the wire conduit 62 (that is, that extends distally from the stopper 64) may be long enough such that the wires 66 lie against the expanded balloon 24 just loosely enough to avoid damaging or distorting the balloon 24 but snugly enough that the wires 66 don't kink or bend, and that sufficient pressure is exerted against the one or more temperature sensors 96 and mapping electrodes 98 against the target tissue when the balloon 24 is in contact with the target tissue. As shown in FIGS. 5 and 6, deployment of the device 12 beyond the sheath 16 essentially everts the wires 66 of the accessory 18, and causes the stopper 64 to extend beyond (distal to) the anchor element 68. If a reference electrode 106 is used, it may be disposed on a wire 66 proximate the anchor element 68, such that the reference electrode 106 is positioned proximal to the expanded balloon 20, thus reducing the likelihood that the reference electrode 106 would be in contact with the target tissue.

Figure 7:
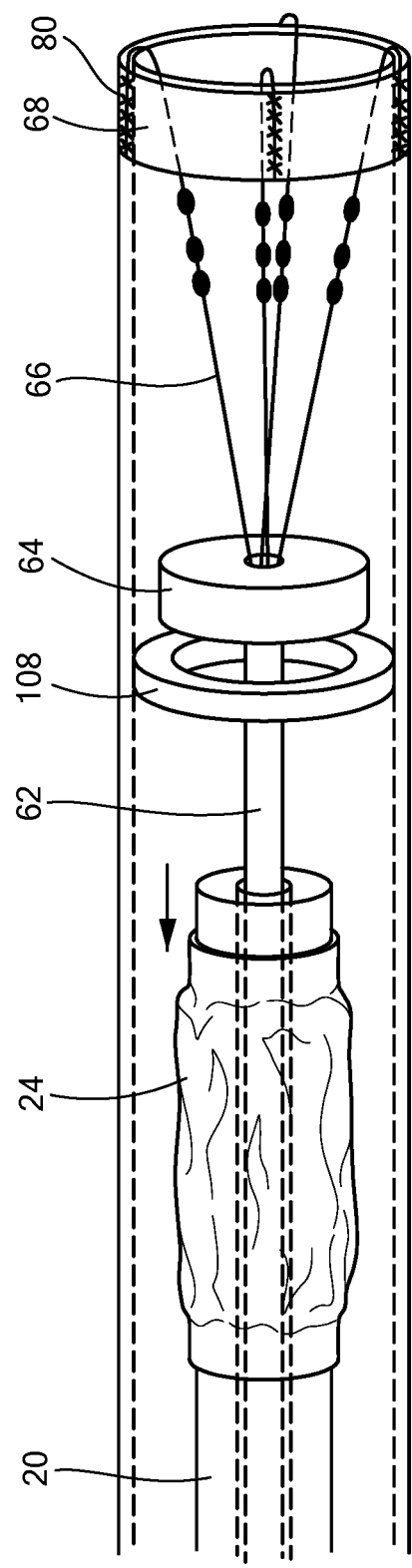

As shown in FIG. 7, the device 12 may be retracted or withdrawn through the sheath 16 toward the proximal portion 107 of the sheath 16. At a certain point within the sheath 16, the device distal tip 48 may become disengaged from the stopper 64 and the device 12 may be removed from the patient's body, leaving the accessory 18 attached to the sheath 42. For example, the inner lumen of the sheath 16 may include a protrusion or ridge 108 that prevents the stopper 64 from retracting further within the sheath 16 but allows passage of the device distal tip 48, thereby causing the device distal tip 48 to disengage. This protrusion or ridge 108 may be a tab-like protrusion from an inner surface of the inner lumen or may be an annular ridge that encircles or partially encircles at least a portion of the inner lumen. Alternatively, the device distal tip 48 may become disengaged from the stopper 64 when the stopper 64 is retracted far enough within the sheath 16 to cause the distal portions 74 of the wires 66 to go taught, the force of which will prevent the stopper 64 from being retracted farther. While the sheath 16 is being removed from the patient's body, the stopper 64 may be retained within the sheath 16 by a gentle pull force exerted on the proximal portions 78 of the wires 66 and/or the proximal portion 72 of the wire conduit 62.

Referring now to FIGS. 8A-9B, close-up views of exemplary embodiments of a stopper of a balloon catheter accessory are shown. As discussed above regarding FIGS. 3-7, the at least a portion of the stopper 64 may have a configuration that is matable with the device distal tip 48 and is used to removably engage the device distal tip 48 with the stopper 64. To facilitate engagement between the stopper 64 and device distal tip 48, the user may apply a counterforce (that is, pulling force) in the stopper 64 against the pushing force of the device distal tip 48 by gently pulling on the proximal portions 78 of the wires 66 and/or the proximal portion 72 of the wire conduit 62, which may be located outside the patient's body. Additionally or alternatively, the wire conduit 62 and the stopper 64 may each include a magnet, such that the two components may be magnetically attracted to each other.

Figure 8A:
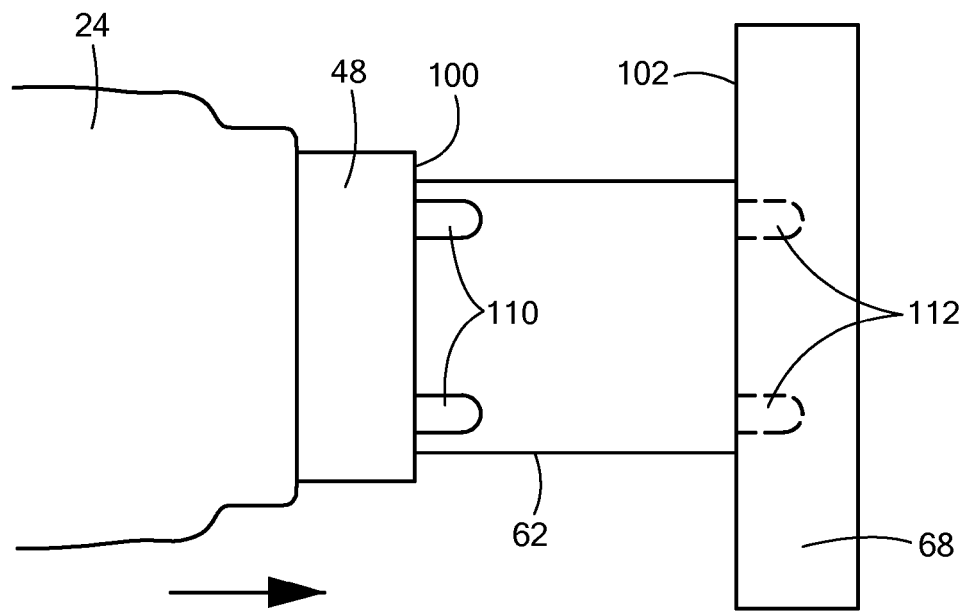
FIGS. 8A and 8B show a close-up view of an exemplary embodiment of a stopper of a balloon catheter accessory.
Figure 8B:
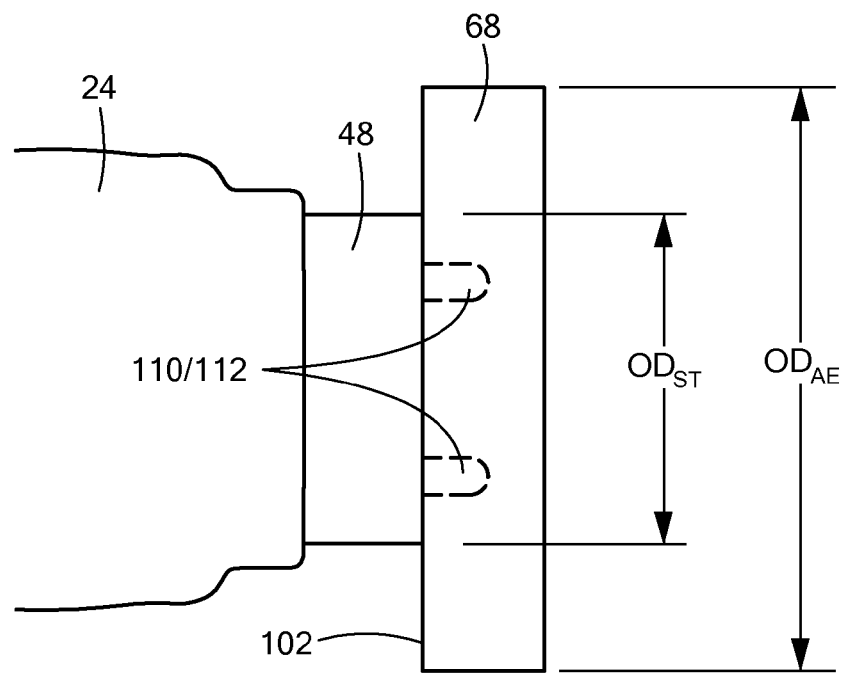

In the non-limiting embodiment shown in FIGS. 3-7, the device distal tip 48 may have a planar or substantially planar annular distal face 100 and the stopper 64 may include a planar or substantially planar annular proximal face 102, both of which being substantially orthogonal to the longitudinal axis 104 of the device 12. In contrast, the non-limiting embodiments shown in FIGS. 8A-9B may include non-planar geometry. For example, as shown in FIGS. 8A and 8B, the annular distal face 100 of the device distal tip 48 may include one or more protuberances 110, which may be, for example, dome-shaped or peg-shaped. Similarly, the annular proximal face 102 of the stopper 64 may include one or more indentations 112 corresponding to the protuberances 110 of the distal face 100 of the device distal tip 48. Thus, the one or more protuberances 110 may be matably engageable with the one or more indentations 112, providing a removable coupling between the device 12 and the accessory 18. To disengage the device 12 from the stopper 64 of the accessory 18, the device 12 may be retracted away from the stopper 64, which will cause the protuberances 110 to separate from the corresponding indentations 112.

Figure 9A:
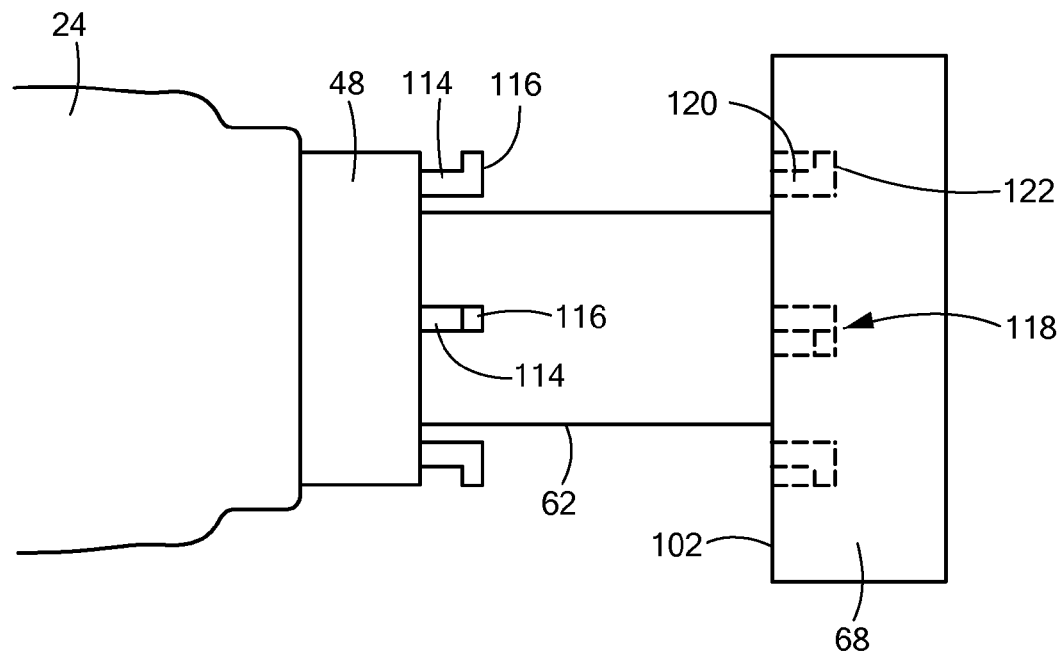
FIGS. 9A and 9B show a close-up view of a further exemplary embodiment of a stopper of a balloon catheter accessory.
Figure 9B:
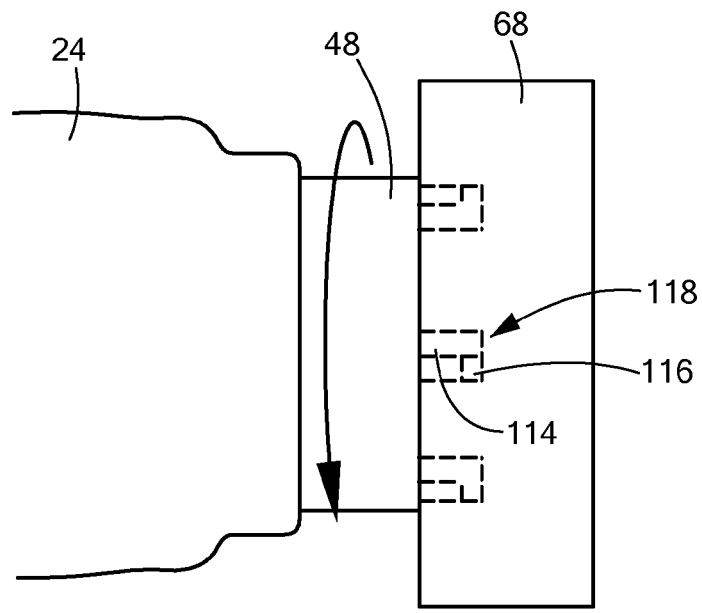

In the non-limiting embodiment shown in FIGS. 9A and 9B, the annular distal face 100 of the device distal tip 48 may include one or more posts 114, each of which including a rounded or angular lip 116 at the distal end. Similarly, the annular proximal face 102 of the stopper 64 may include one or more L-shaped or curved tracks 118 configured to receive and lock the lip 116 of each post 114 within the track 118. For example, the device 12 may be advanced over the wire conduit 62 toward the stopper 64 until each post 114 of the device distal tip 48 matably engages with a portion 120 of the corresponding track 118 that is substantially parallel to the longitudinal axis 104 of the device 12. Then, the device 12 may be rotated in the direction to which the substantially transverse portion 122 of the corresponding track 118 is extended. This rotation may lock the device 12 to the stopper 64 of the accessory 18. To disengage the device 12 from the accessory 18, the device 12 may be rotated in the opposite direction and the posts 114 may be retracted from the longitudinal portion 120 of the track 118.

Figure 10:
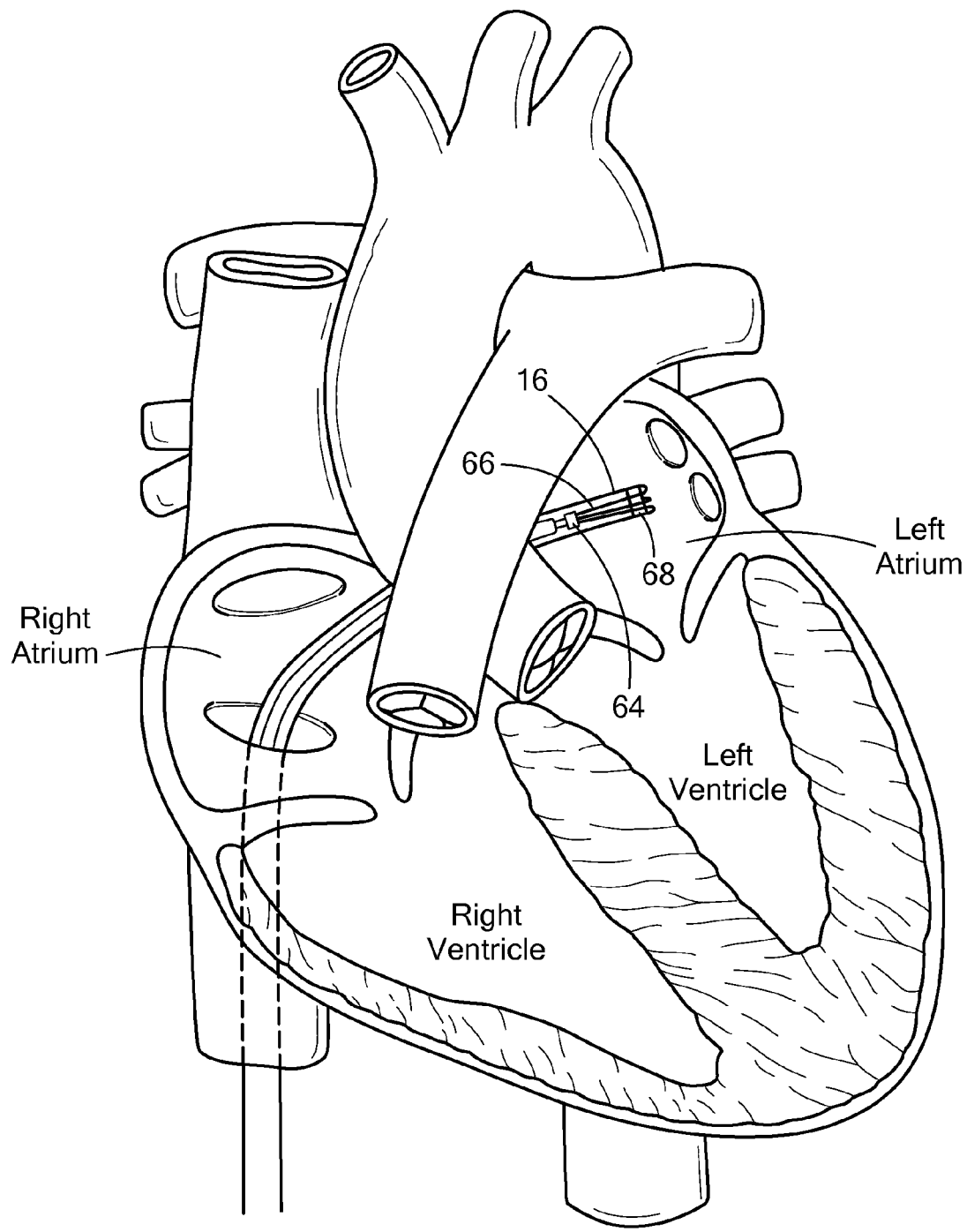
FIGS. 10-14 show a series of steps for deploying a balloon catheter in use with a balloon catheter accessory in a patient's heart.

Referring now to FIGS. 10-14, a series of steps for deploying a balloon catheter in use with a balloon catheter accessory in a stylized rendering of a patient's heart is shown. The steps shown in FIGS. 10-14 are generally the same as those of FIGS. 3-7, but are shown within the heart at a non-limiting example of a target treatment site, the left atrium. As shown in FIG. 10, the sheath 16 with attached accessory 18 may be passed through the patient's vasculature and positioned at a location proximate a target treatment site. For example, the sheath 16 and accessory 18 are shown in the left atrium. Although FIG. 10 shows the left atrium having been accessed through puncture of the septum between the right atrium and the left atrium, it will be understood that other methods of accessing the left atrium may be used, and target treatment sites other than the left atrium may be desired.

Figure 11:
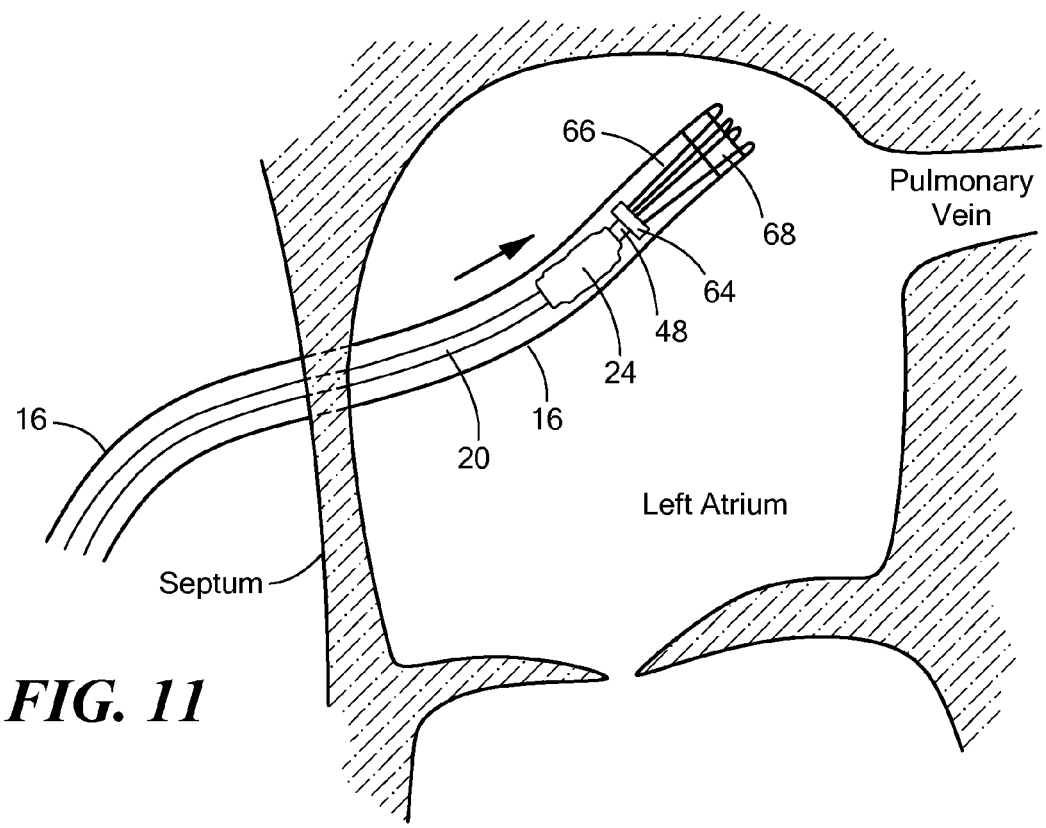
Figure 12:
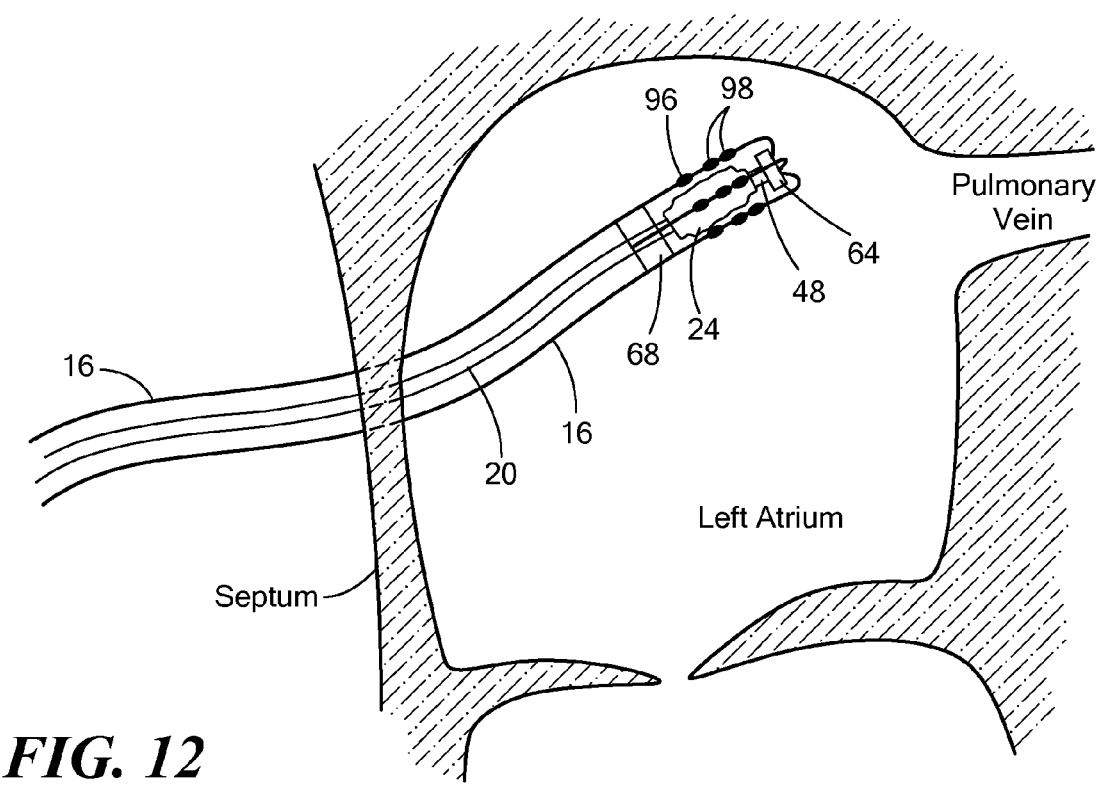
Figure 13:
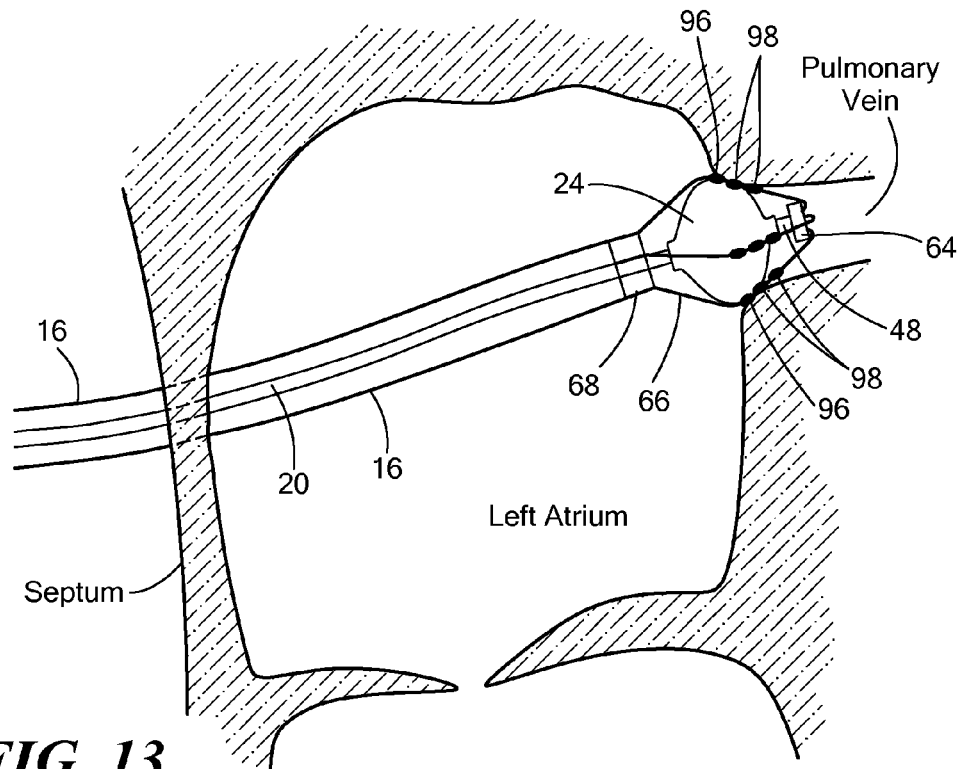

As shown in FIG. 11 (showing a close-up view of the left atrium), the device 12 may be advanced within the sheath 16 over the wire conduit 62 until the device distal tip 48 comes into contact with the stopper 64 and, depending on the configurations of the distal face 100 of the device distal tip 48 and proximal face 102 of the stopper 64, the device 12 matably engages with the accessory 18. The device 12 then continues to be advanced within the sheath 16 until the balloon 20 is outside the sheath 16 (as shown in FIG. 12). In this step, the plurality of wires 66 may become everted and may extend proximally over the outer surface of the balloon 20 from the stopper 64 to the anchor element 68. As shown in FIG. 13, the balloon 20 may be inflated, for example, by initiating or increasing the flow of coolant or other fluid from the fluid supply 52 into the interior chamber 40 of the balloon 20. The inflated and expanded balloon 20 may provide pressure against the inner surfaces of the one or more temperature sensors 96 and/or the one or more mapping electrodes 98 to enhance contact between the outer surfaces of the one or more temperature sensors 96 and/or the one or more mapping electrodes 98 and the target myocardial tissue. Once the balloon 20 is inflated, the control unit 14 may receive temperature measurement signals from the one or more temperature sensors 96 and/or mapping signals from the one or more mapping electrodes 98. Thus, the accessory 18 may provide temperature sensing and/or mapping functionality to a standard balloon catheter 12 without the complication of attaching or integrating the sensors 96 and/or mapping electrodes 98 to the device 12 itself.

Figure 14:
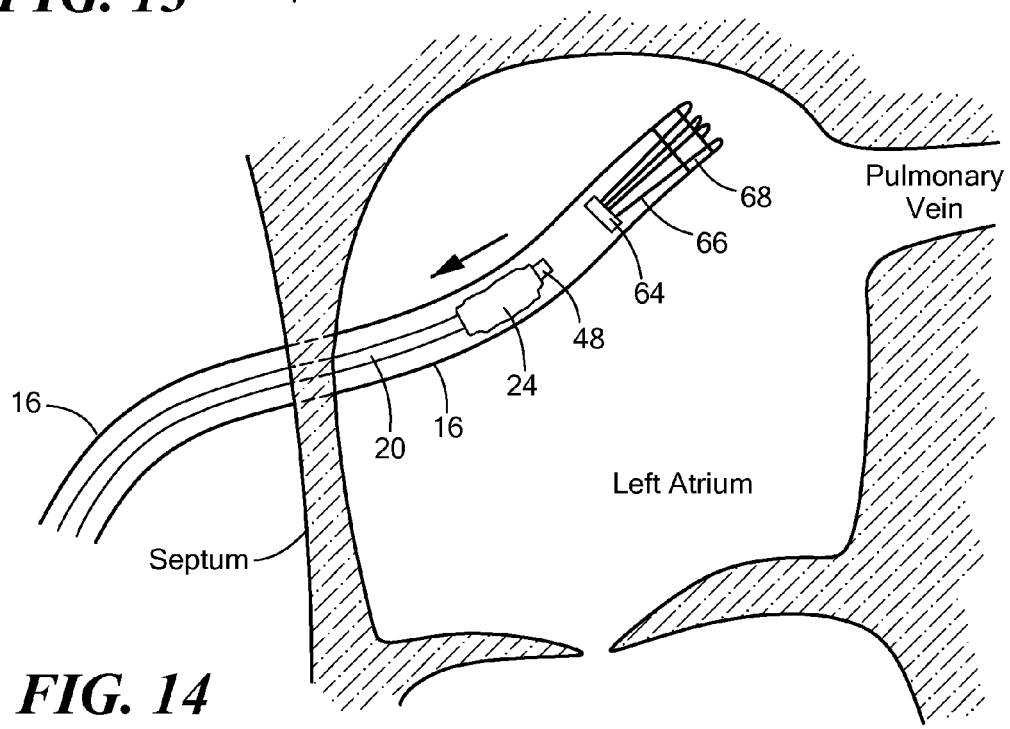

As shown in FIG. 14, the device 12 may be retracted or withdrawn through the sheath 16 toward the proximal portion 107 of the sheath 16 for removal of the device 12 from the patient's body. At a certain point within the sheath 16, the device distal tip 48 may become disengaged from the stopper 64, as shown and described in FIG. 7. The device 12 may first be completely removed from the patient's body and from within the sheath 16, followed by removal of the sheath 16 with attached accessory 18 from the patient's body. Alternatively, the device 12 may be retracted to a certain distance within the sheath 16, and the sheath 16 with attached accessory 18 and the device 12 may together be removed from the patient's body.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system for evaluating tissue, the system comprising:
   an elongate sheath having a proximal portion, a distal portion, and a lumen therebetween;
   a medical device including an inflatable element at a distal portion of the medical device and a distal tip, the medical device being slidably movable within the sheath such that the inflatable element and distal tip are positionable beyond the distal portion of the sheath;
   a first annular element coupled to an outer surface of the distal portion of the sheath;

a plurality of wires coupled to the first annular element, at least one of the plurality of wires including at least one sensor element;

an elongate wire conduit disposed within the lumen of the sheath, the wire conduit having a proximal portion, a distal portion, and a lumen therebetween; and a second annular element coupled to the distal portion of the wire conduit, at least a portion of each of the plurality of wires passing through the second annular element and being disposed within the lumen of the wire conduit, when the inflatable element and distal tip are beyond the distal portion of the sheath and the inflatable element is inflated, the distal tip is engaged with the second annular element and the plurality of wires are disposed over an outer surface the inflatable element.

2. The medical system of claim 1, wherein the plurality of wires includes four wires.

3. The medical system of claim 1, wherein the sheath lumen is sized to receive a balloon catheter therein when the balloon is in a deflated state.

4. The medical system of claim 1, wherein the at least one sensor element includes at least one of a temperature sensor and a mapping electrode.

5. The medical system of claim 4, wherein at least one of the plurality of wires includes a mapping electrode and at least one of the plurality of wires further includes a reference electrode.

6. The medical device of claim 4, wherein each of the plurality of wires includes at least one temperature sensor and at least one mapping electrode.

7. The medical system of claim 1, wherein the first annular element includes a distal edge, a proximal edge, an inner surface, and an outer surface, and each of the plurality of wires include a proximal portion and a distal portion.

8. The medial system of claim 7, wherein a first portion of the distal portion of each of the plurality of wires is coupled to the outer surface of the first annular element, a second portion of the distal portion of each of the plurality or wires passes over the distal edge of the annular element, and a third portion of the distal portion of each of the plurality of wires passes within the annular element proximate the inner surface of the annular element.

9. The medical system of claim 1, wherein the second annular element includes a proximal face and a distal face, the proximal face being configured to be releasably engageable with a distal tip of a medical device.

10. The medical system of claim 1, further comprising a control unit including a processor, the processor being configured to receive signals from the at least one sensor element.

11. The medical system of claim 10, wherein the processor causes the control unit to generate an alert based at least in part on signals received from the at least one sensor element.

* * * * *